United States Patent [19]

Chester et al.

[11] 4,351,979
[45] * Sep. 28, 1982

[54] MANUFACTURE OF AROMATIC COMPOUNDS

[75] Inventors: Arthur W. Chester; Yung F. Chu, both of Cherry Hill, N.J.

[73] Assignee: Mobil Oil Corporation, New York, N.Y.

[*] Notice: The portion of the term of this patent subsequent to Aug. 11, 1998, has been disclaimed.

[21] Appl. No.: 256,872

[22] Filed: Apr. 24, 1981

Related U.S. Application Data

[63] Continuation-in-part of Ser. No. 140,346, Apr. 14, 1980, Pat. No. 4,283,584.

[51] Int. Cl.³ .............................................. C07C 5/22

[52] U.S. Cl. .................................... 585/481; 585/488; 208/66

[58] Field of Search .................. 585/481, 488; 208/66

[56] References Cited

U.S. PATENT DOCUMENTS 4,236,996  12/1980  Tabak et al. ........................ 208/134
4,283,584   8/1981  Chester et al. ...................... 585/481

*Primary Examiner*—Curtis R. Davis
*Attorney, Agent, or Firm*—Charles A. Huggett; Michael G. Gilman; Charles J. Speciale

[57] ABSTRACT

Isomerization of xylene admixed with other alkyl aromatics of at least eight carbon atoms and with normal or slightly branched paraffins is conducted at 600°–800° F. with a zeolite like zeolite ZSM-5 of reduced acid activity.

23 Claims, No Drawings

MANUFACTURE OF AROMATIC COMPOUNDS

CROSS REFERENCE TO RELATED APPLICATIONS

This application is a continuation-in-part of copending application Ser. No. 140,346, filed Apr. 14, 1980, now U.S. Pat. No. 4,283,584 and is also related to copending application Ser. No. 230,916, filed Feb. 2, 1981.

FIELD OF THE INVENTION

The invention is concerned with manufacture of aromatic compounds having six ($C_6Ar$) to eight ($C_8Ar$) carbon atoms, namely benzene, toluene and xylene (BTX). At the present time, the most valuable of these is p-xylene, which may be separated for use in synthesis of polyesters from mixed xylenes by fractional crystallization. Also highly valued is benzene for use as chemical raw material. Toluene is also valuable for varied uses as solvent, in chemical manufacture and as a high octane gasoline component.

According to the present invention, available raw materials such as reformed petroleum naphthas (reformate) are processed to yield p-xylene as the principal product and to produce toluene and benzene as substantially the sole aromatic by-products.

BACKGROUND OF THE INVENTION

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./ U.S. Gal. |
|---|---|---|---|
| Ethylbenzene | −139.0 | 277.0 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources may vary quite widely in composition but will usually be in the range 10 to 32 wt.% ethylbenzene with the balance, xylenes, being divided approximately 50 wt.% meta, and 25 wt.% each of para and ortho.

Individual isomer products may be separated from the naturally occurring mixtures by appropriate physical methods. Ethylbenzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes, as by OCTAFINING.

In a typical plant for utilization of Octafining, a mixture of $C_8$ aromatics is introduced to an ethylbenzene tower wherein the stream is stripped of a portion of its ethylbenzene content, to an extent consistent with retaining all the xylenes in the feed stream without unduly expensive "superfractionation". Ethylbenzene is taken overhead while a bottom stream, consisting principally of xylenes, together with a significant amount of ethylbenzene, passes to a xylene splitter column. The bottoms from the xylene splitter constituted by o-xylene and $C_9$ aromatics passes to the o-xylene tower from which o-xylene is taken overhead and heavy ends are removed. The overhead from the xylene splitter column is transferred to conventional crystallization separation. The crystallizer operates in the manner described in Machell, et al., U.S. Pat. No. 3,662,013 dated May 9, 1972.

Because it's melting point is much higher than that of the other $C_8$ aromatics, p-xylene is readily separated in the crystallizer after refrigeration of the stream and a xylene mixture lean in p-xylene is transferred to an isomerization unit. The isomerization charge passes through a heater, is admixed with hydrogen and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product constituted by $C_8+$ hydrocarbons is recycled in the system to the inlet of the xylene splitter.

It will be seen that the system is adapted to produce quantities of p-xylene from a mixed $C_8$ aromatic feed containing all of the xylene isomers plus ethylbenzene. The key to efficient operation for that purpose is in the isomerizer which takes crystallizer effluent lean in p-xylene and converts the other xylene isomers in part to p-xylene for further recovery at the crystallizer.

Among the xylene isomerization processes available in the art, Octafining was originally unique in its ability to convert ethylbenzene. Other xylene isomerization processes have required extremely expensive fractionation to separate that component of $C_8$ aromatic fractions. As will be seen from the table of properties above, the boiling point of ethylbenzene is very close to those of p and m-xylene. Complete removal of ethylbenzene from the charge is impractical. The usual expedient for coping with the problem was an ethylbenzene separation colum in the isomerizer-separator loop when using catalyst other than those characteristic of Octafining. It will be seen that Octafining does not need this expensive auxiliary to prevent build up of ethylbenzene in the loop. This advantageous feature is possible because the Octafining catalyst converts ethylbenzene.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethane and benzene and hydrocracking of alkyl cyclohexanes.

A significant improvement arose with the introduction of catalysts such as zeolite ZSM-5 combined with a metal such as platinum as described in Morrison U.S. Pat. No. 3,856,872. At temperatures around 700°–800° F., ethylbenzene is converted by disproportionation over this catalyst to benzene and diethylbenzene. At higher temperatures and using a zeolite ZSM-5 catalyst of reduced activity, ethylbenzene and other single ring aromatics are converted by splitting off side chains of two or more carbon atoms as described in U.S. Pat. No. 4,188,282.

These developments permit upgrading of Octafining reactors by substitution of the improved (ZSM-5) catalyst.

In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further advance in the art is described in patents to Morrison and Tabak directed to various techniques for reducing acid activity of zeolite ZSM-5 catalyst and use of such low activity catalysts for xylene isomerization concurrently with ethylbenzene conversion at temperatures upwards of 800° F. One such patent is U.S. Pat. No. 4,163,028 which discloses xylene isomerization and ethylbenzene conversion at high temperature with ZSM-5 of very high silica/alumina ratio whereby the acid activity is reduced.

The inventions of those patents are predicated on discovery of combinations of catalyst and operating conditions which decouples ethylbenzene conversion from xylene loss in a xylene isomerization reaction, thus permitting feed of $C_8$ fractions which contain ethylbenzene without sacrifice of xylenes to conditions which will promote adequate conversion of ethylbenzene. These results are obtained by use of a catalyst characterized by zeolite ZSM-5 substantially reduced in activity as by dilution, steaming, very high silica/alumina ratio, base exchange with alkali metal, coking or the like. At the high temperatures of 800°–1000° F., the zeolite of reduced activity exhibits effective power for isomerization of xylene and for splitting off alkyl side chains of two or more carbon atoms from single ring aromatics at long on-stream periods. The disproportionation activity of the zeolite is severely depressed by the reduced acid activity, resulting in low losses of xylene by that mechanism. That lack of disproportionation activity impairs the capacity of the catalyst to handle trialkyl aromatics of nine or more carbon atoms, e.g. trimethylbenzene, as practiced in some processes. It thus becomes necessary to remove from the recycle stream those components having more than eight carbon atoms to avoid excessive build-up in the system of $C_9$ and higher. The catalyst also has the capacity to crack paraffins in the charge to lower boiling compounds readily removable from recycle streams by fractionators normally present in the p-xylene recovery/isomerizer loop.

By reason of this combination of activities, the catalyst may be used in a system charging reformate without removal of paraffin hydrocarbons as described in U.S. Pat. No. 4,211,836.

In prior copending application Ser. No. 140,346 filed Apr. 4, 1980, it is shown that such processes charging unextracted reformate are improved by the addition of paraffins having no more branching than a single methyl group on any carbon atom of the paraffin chain, e.g., n-nonane. The entire disclosure of prior application Ser. No. 140,346 is incorporated herein by this reference.

SUMMARY OF THE INVENTION

It has now been found that such normal and slightly branched paraffins may be included in the charge to lower temperature xylene siomerization over low acidity zeolites similar to ZSM-5 plus a metal when the charge is substantially free of more highly branched paraffins, for example, extracted $C_8$ reformate plus n-nonane.

DESCRIPTION OF THE SPECIFIC EMBODIMENTS

The essence of the invention is the efficient isomerization reactor which can also serve for selective dealkylation of single ring aromatic compounds to remove alkyl side chains of two or more carbon atoms. That reactor is characterized by a zeolite catalyst having a silica/alumina ratio of at least 12, a constraint index as defined in Ser. No. 140,346 between about 1 and 12 and a reduced acid activity defined below. The zeolite catalyst is combined with a hydrogenation metal from Group VIII of the Periodic Table, e.g. cobalt, nickel, platinum, palladium, etc. The reactor is maintained at a temperature of 600° to 800° F. and a pressure above about 100 pounds per square inch, gauge (psig). Very high pressures require excessively expensive facilities and are generally avoided for economic reasons although it does not appear that such pressures have any adverse effect on the reaction. For the reason stated, pressures employed will generally be not greater than 2000 psig.

The reactor of this invention may be incorporated in a reaction train through which a petroleum naphtha is processed for manufacture of p-xylene. Alternatively, the process of the invention may be used in a facility charging purchased $C_8$ aromatics or mixed xylenes. Typically a light petroleum naphtha is supplied to a catalytic reformer operated to convert naphthenes to aromatics by dehydrogenation under hydrogen pressure over a catalyst of platinum supported on alumina.

The aromatic rich reformate product of the reformer is fractionated to separate compounds of about eight carbon atoms ($C_8$) which is then extracted with a suitable selective solvent to separate aromatics from paraffins and provide a $C_8$ aromatics fraction. The $C_8$ aromatic fraction prepared by the solvent extraction stage may be fractionated for removal of some ethylbenzene. The degree of ethylbenzene removal, if practiced, may be accommodated to the desires of the operator, since the reactor of this invention can tolerate considerable amounts of ethylbenzene, which is thereby converted to benzene.

In any event, fresh feed to the isomerizer contains the $C_8$ aromatic fraction from a solvent extraction stage and containing some ethylbenzene. The feed will contain the xylenes generated by reforming in association with more or less aromatics boiling in the xylene range or higher. A stream of normal or slightly branched paraffins is added to the charge for the reactor which is operated under hydrogen pressure.

Under the high temperature conditions prevailing in the reactor, that catalyst has capacity (1) to isomerize xylenes thereby restoring equilibrium concentrations in the mixed xylenes of the feed to generate additional p-xylene, (2) to remove alkyl chains of two or more carbon atoms from single ring aromatics, leaving methyl groups to thereby generate BTX, and (3) to crack normal paraffins to lower boiling compounds which can be removed in the downstream fractionators. The invention therefor contemplates adding to the feed for the reactor of streams which contain paraffins of straight or slightly branched character.

The effluent of the reactor contains the three xylenes in proportions approaching the thermodynamic equilibrium value together with conversion products from reaction of ethylbenzene and higher boiling alkyl aromatics as well as a portion of unreacted ethylbenzene and higher. The by-products will include benzene, toluene and xylenes derived by reactions of such compounds as ethylbenzene, methylethylbenzene, dimethylethylbenzene, etc. The reaction mixture is fractionated to take compounds of five carbon atoms and less overhead, benzene and toluene as a side stream and bottoms substantially constituted by aromatics of eight or more carbon atoms. That bottoms fraction is then fractionated to remove aromatics of nine or more carbon atoms as bottoms. The overhead fraction of eight carbon atom aromatics is transferred as feed to a p-xylene separator of conventional design.

The reactor of this invention contains a crystalline alumino-silicate (zeolite) catalyst of relatively low acidity. That catalyst promotes a reaction course which is unique at temperatures of 600° to 800° F. Ethylbenzene in the charge is selectively cracked to benzene at little or no conversion of xylenes. Two or more carbon atom chains on other aromatics undergo like conversion. The two types of conversion are decoupled such that reaction severity is not a compromise to achieve effective ethyl aromatic conversion at "acceptable" loss of xylene. This characteristic of the process renders unnecessary the preliminary distillation to separate at least some of the ethylbenzene and $C_9+$ aromatics from the feed stream as practiced in prior processes. At the temperatures characteristic of this invention, the catalyst will not crack substantial amounts of isoparaffins having greater branching than single methyl groups and extraction of paraffins from the fresh reformate charge is necessary.

According to the present invention, normal and slightly branched paraffins are added to the reactor charge. The term "slightly branched" refers to paraffins in which no carbon atom bears substituents in excess of a single methyl group.

Particularly preferred catalysts for the reactor are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain a degree of crystallinity for long periods in spite of the presence of steam at high temperature which includes irreversible collapse of the framework of other zeolites, e.g. of the X and A type. Furthermore, carbonaceous deposits when formed, may be removed by burning at higher than usual temperatures to restore activity. In many environments the zeolites of this class exhibit very low coke forming capability, conductive to very long times on stream between burning regenerations.

An important characteristic of the crystal structure of this class of zeolites is that it provides constrained access to, and egress from the intracrystalline free space by virtue of having a pore dimension greather than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedron. Briefly, the preferred type zeolites useful in this invention possess, in combination, a silica to aluminia mole ratio of at least about 12; and a structure providing constrained access to the crystalline free space.

In one embodiment, the desired low activity is achieved by unusually high silica/alumina ratio, greater than 200, preferably above 500.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type of zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methyl pentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above-constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variables extremes.

While the above experimental procedure will enable one to achieve the desired overall conversion of 10 to 60% of most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The specific zeolites described, when prepared in the presence of organic cations, are catalytically inactive, possibly because of intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-35, and ZSM-38, with ZSM-5 or its metal containing variant particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 30 and a dried crystal density of not less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |

| Zeolite | Void Volume | Framework Density |
|---|---|---|
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with the porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The invention utilizes zeolites of the type described, limited however to those forms which are of relatively low acidity. It has been found that, as the acid activity of these zeolites is reduced, the capacity to catalyze disproportionation declines without substantial decline in the capacity to catalyze dealkylation of such compounds as ethylbenzene having side chains of two or more carbon atoms. The invention takes advantage of that unique characteristic to achieve the processing advantage that isomerization is decoupled from ethylbenzene conversion which now proceeds by dealkylation in the presence of the low acidity zeolite. A significant consequence of these catalytic properties is that recycle of toluene and trimethylbenzene to the reactor is generally undesirable. The lack of disproportionation activity means that these methylbenzenes will not be converted in significant amounts to xylenes. Hence recycle of these unreactive species results in undesirable build-up in the loop of diluent materials.

The low acid activity of the catalyst is attainable in any of several ways or a combination of these. An alternative is to form the zeolite at high silica/alumina ratio above 200, preferably above 500. Very high dilution with an inert matrix is also effective. For example, composites of a more active form of zeolite ZSM-5 with alumina at a ratio of 5 parts of zeolite with 95 parts of the inert matrix provides a suitable catalyst.

Activity of these zeolites is preferably reduced to levels suited to practice of the invention by treatment with steam at high temperature as described in U.S. Pat. No. 3,965,209. Zeolites employed in such severe reactions as aromatization of paraffins and olefins lose activity to an extent which makes them suitable for use in the process of this invention. See U.S. Pat. No. 3,960,978 for fuller discussion of this manner of deactivated zeolite. Another method for reducing activity is to provide basic cations such as sodium at a significant proportion of the cationic sites of the zeolite. That technique is described in U.S. Pat. No. 3,899,544.

In many cases, steaming will be the preferred manner of reducing the acid activity of the zeolite catalyst. That catalyst preparation step may be conducted by passing steam at suitable temperature, generally 1000° F. or higher through the catalyst for a period of several hours until the desired reduction in disproportionation activity is achieved.

By whatever means the reduced acid activity is achieved, the activity may be measured in terms of disproportionation activity. A suitable test for the purpose involves contacting xylenes in any convenient mixture or as a single pure isomer over the catalyst at 900° F., 200 psig and liquid hourly space velocity (LHSV) of 5. Suitable catalysts for use in the process of the invention will show a single pass loss of xylenes (by disproportionation) of less than 2 weight percent, preferably less than one percent. It is this very low rate of disproportionation at very high levels of ethylbenzene conversion to benzene (about 30%) that provides the advantage of the new chemistry of aromatics processing characteristic of the invention. That lack of disproportionation (and transalkylation generally) activity also dictates withdrawal of compounds boiling above and below eight carbon atom aromatic compounds. For example, toluene and trimethylbenzene are converted to very little, if any, extent and become diluents which occupy reactor space to no advantage. Small amounts of such diluents can be tolerated, such as those present by reason of "sloppy" fractionation, but withdrawal to at least a major extent is important to efficient operation.

Little differences in process chemistry is found with ZSM-5 catalyst of low activity achieved by techniques other than steaming, though tests of these showed higher aging rates as measured by the temperature increase required to maintain constant ethylbenzene conversion.

It is considered preferable for purposes of this invention to steam the catalyst prior to use in the process of this invention to control its acid activity. In particular, the unsteamed catalyst, which may be referred to herein as the precursor catalyst, is steamed under relatively mild conditions, such as for about one to about ten hours with 100% steam at atmospheric pressure and at a temperature of about 800° F. to 1000° F. to reduce its acidity to a measured "Alpha" value in the range of 45 to 110. It is to be understood, of course, that the treating conditions may be altered from those recited, such as by using superatmospheric pressure at reduced temperature, the critical parameter being the controlled acidity of the steamed catalyst. In any case, however, sufficient steam treatment is required to reduce Alpha by at least 10 (ten).

The controlled acid activity of the catalyst is conveniently defined by the "Alpha" scale described in an article published in Journal of Catalysis, Vol. VI, pp 278–287 (1966) which publication is incorporated herein by reference. In this test, the catalyst is contacted with hexane under prescribed conditions and the amount of hexane which is cracked is measured. From this measurement is computed the "Alpha" value used herein. For purposes of the present invention, however, all measurements of "Alpha" are to be made at 1000° F., and all references to "Alpha" are to understood to refer to the value obtained when the hexane cracking is measured at 1000° F.

In general, it is desirable to operate the process of this invention in the presence of hydrogen gas to extend catalyst life and maintain good efficiency. The hydrogen to hydrocarbon mole ratio may be from 0.1 to 10, and preferably from 0.5 to 5.0, with a total pressure from about atmospheric up to 1000 psig. The space velocity is usually adjusted to provide a desired conversion of ethylbenzene per cycle, usually from about 20 to 40%, and with at least 98% para approach to equilibrium.

THE PARAFFIN ADDITIVE

It will be recognized from the foregoing discussion that charge fractions contemplated by the invention will not contain isoparaffinic hydrocarbons as constituents of a reformate fraction which has been extracted to separate those compounds. The paraffins so removed from the reformate fraction will be constituted by mixtures of isomers approximating the thermodynamic equilibrium because the reforming catalyst of platinum on silica-alumina is a powerful isomerization catalyst. For purposes of this invention, the isomerizer feed will contain 1 to 25 weight percent of added paraffins which are normal or which have no carbon atom with substituents in excess of a single methyl group. Those paraffins preferably are in the range of three to twelve carbon atoms, with n-nonane being particularly preferred. Paraffins of more than six carbon atoms give best results.

Such concentration of this limited class of paraffins are not found in extracted reformates and it is necessary, in practice of the invention to add a stream containing the paraffin additive. The additive may be introduced at any point in the system which will result in the desired concentration in the reactor feed. It is preferable to add the paraffins directly to the reactor feed in order that they shall not increase the load on fractionators, the separator and other equipment upstream of the reactor.

The benefits of the invention were demonstrated by a series of once-through runs on a pilot plant for isomerization of a synthetic feed stock shown in Table I which also reports conditions and results of those runs over a platinum/ZSM-5 catalyst prepared in the manner described below.

CATALYST PREPARATION

HZSM-5 crystalline zeolite powder having a 70:1 silica/alumina ratio is contacted with a solution of tetramine platinum chloride in an amount calculated to deposit 0.1 wt. % of platinum on the final catalyst. An amount of Alpha-alumina mono-hydrate is added to the zeolite to provide a final catalyst having about 50 wt. % content of zeolite on an anhydrous basis. The zeolite and matrix are intimately mixed and tempered with water and extruded to form pellets. The pellets are dried and then they are calcined in nitrogen to remove the organics. Then they are exchanged with aqueous ammonium nitrate to reduce the sodium content to below 0.05 wt. %. The exchanged pellets are dried and then calcined again in air.

A portion of the calcined pellets are exposed to 100% steam at atmospheric pressure and at a temperature of 900° F. for 4.5 hours. The Alpha value of the steamed catalyst, measured at 1000° F., was 60.

EXAMPLES

The catalyst so prepared was charged to a pilot plant reactor and a series of five runs at different conditions specified in Table I were conducted over a total of 82.3 hours. In these runs, the synthetic feed shown in the first column of Table I was a blend of ethylbenzene and xylenes deficient in the para and ortho isomers containing about 3% each of iso-octane and n-nonane. It will be seen that the n-nonane was extensively converted while the iso-octane remained substantially unchanged. It will be clear that iso-paraffins in the charge to such an operation in a loop will build up on each cycle through the loop. The approach of p-xylene to equilibrium values is very favorable and the conversion of ethylbenzene is very good. Of particular interest is the ratio of benzene made to ethylbenzene converted ($\Delta BZ/\Delta EB$ MOLAR RATIO). Those values demonstrate that the chemistry of ethylbenzene conversion is primarily dealkylation.

TABLE I

| XYLENE ISOMERIZATION WITH STEAMED ZSM-5 PARAFFINS ADDED | | | | | | |
|---|---|---|---|---|---|---|
| EXAMPLE NO. | | 1 | 2 | 3 | 4 | 5 |
| Temperature, °F. | | 690 | 700 | 720 | 750 | 650 |
| Pressure, psig | | 100 | 100 | 100 | 100 | 100 |
| WHSV | | 6.9 | 9.9 | 13.9 | 14.0 | 5.0 |
| H2/HC Molar Ratio | | 2.1 | 2.0 | 2.0 | 2.0 | 2.0 |
| Time on Stream, Hrs. | | 19.0 | 39.0 | 59.5 | 63.0 | 82.3 |
| EB Conversion, Wt. Pct. | | 37.7 | 31.2 | 30.0 | 42.7 | 21.3 |
| I-C8 Conv., Wt. Pct. | | 1.3 | 1.0 | 2.0 | 2.7 | −2.1 |
| N-C9 Conv., Wt. Pct. | | 77.4 | 58.0 | 50.0 | 61.3 | 51.3 |
| Xylene Loss, Wt. Pct. | | 2.0 | 1.2 | 1.1 | 1.2 | 1.5 |
| Ring Loss, Mol Pct. | | 0.0 | −0.1 | −0.3 | −0.2 | −0.3 |
| Equilibrium Approach | | | | | | |
| P-xylene | | 104.9 | 105.1 | 103.6 | 106.4 | 103.9 |
| M-xylene | | 98.3 | 96.7 | 96.3 | 97.0 | 98.0 |
| O-xylene | | 92.6 | 89.6 | 90.2 | 89.4 | 92.8 |
| C2=/C2 Molar Ratio | | 0.00 | 0.00 | 0.00 | 0.00 | 0.00 |
| C2/ΔEB Molar Ratio | | 0.76 | 0.72 | 0.71 | 0.85 | 0.55 |
| ΔBZ/ΔEB Molar Ratio | | 0.89 | 0.84 | 0.92 | 0.89 | 0.92 |
| H2 Balance | | 98.4 | 99.3 | 98.3 | 98.7 | 97.7 |
| Carbon Balance | | 98.2 | 99.0 | 98.2 | 98.3 | 98.1 |
| Ring Balance | | 98.1 | 99.0 | 98.5 | 98.4 | 98.2 |
| C2 Balance | | 98.8 | 98.7 | 97.6 | 98.7 | 98.3 |
| Total Balance | | 98.1 | 98.9 | 98.1 | 98.2 | 98.0 |
| Prod. Dist. Wt. Pct. | Feed | | | | | |
| C1-C4 N.A.* | | 3.2 | 2.3 | 1.9 | 2.9 | 1.6 |
| C5-C9 N.A.** | | 0.4 | 0.3 | 0.2 | 0.3 | 0.3 |
| I-C8 | 3.1 | 3.0 | 3.0 | 3.0 | 2.9 | 3.1 |
| N-C9 | 3.2 | 0.7 | 1.3 | 1.5 | 1.2 | 1.5 |
| Benzene | | 3.5 | 2.8 | 2.8 | 4.0 | 2.0 |
| Toluene | | 0.6 | 0.4 | 0.4 | 0.7 | 0.3 |
| EB | 14.7 | 8.7 | 9.9 | 9.8 | 8.2 | 11.0 |

TABLE I-continued

XYLENE ISOMERIZATION WITH
STEAMED ZSM-5 PARAFFINS ADDED

| EXAMPLE NO. | 1 | 2 | 3 | 4 | 5 |
|---|---|---|---|---|---|
| P-xylene | 9.6 | 18.9 | 19.0 | 19.0 | 19.0 |
| M-xylene | 63.3 | 41.7 | 42.1 | 42.3 | 41.8 |
| O-xylene | 6.1 | 17.5 | 17.3 | 17.6 | 17.6 |
| C9 + Arom. | | 1.9 | 1.5 | 1.3 | 1.3 |
| Total | 100.0 | 100.0 | 100.0 | 100.0 | 100.0 |

*Non-aromatic
**Net make of non-aromatics, $C_5$–$C_9$ non-aromatics other than iso-octane and n-nonane.

What we claim is:

1. In a process for isomerizing the xylene content of a charge consisting essentially of eight carbon atom aromatic hydrocarbon compounds which mixture contains xylene, and ethylbenzene by contact at conversion conditions under hydrogen pressure with a catalyst comprising a zeolite having a silica/alumina ratio greater than 12 and a constraint index of 1 to 12, the improvement resulting in conversion of ethylbenzene to benzene which comprises adding to the charge 1 to 25 weight percent based on total charge of paraffin hydrocarbons having 3–12 carbon atoms and having no branching in excess of one methyl group on any carbon atom whereby the charge consists essentially of said eight carbon atom aromatic compounds and said paraffinic hydrocarbons, maintaining the conversion temperature between about 600° F. and about 800° F. and using such catalyst comprising a zeolite of reduced acidity such that less than 2 weight percent of xylene is converted to compounds other than xylene when contacted with said catalyst at 900° F., 200 psig and LHSV of 5.

2. A process according to claim 1, wherein said zeolite is in the acid form.

3. A process according to claim 1, wherein said zeolite is ZSM-5.

4. A process according to claim 1, wherein said zeolite comprises alkali metal cations.

5. A process according to claim 1, wherein the concentration of said paraffin hydrocarbon is about 3%.

6. A process according to claim 1, wherein said zeolite is ZSM-5 which has been steamed.

7. A process according to claim 6, wherein the zeolite has been steamed to an Alpha value of 45 to 110.

8. A process according to claim 1, wherein the paraffin hydrocarbon is n-nonane.

9. A process according to claim 1, wherein the catalyst also contains a Group VIII metal.

10. A process according to claim 1, wherein said silica/alumina ratio is greater than 200.

11. A process according to claim 1, wherein said silica/alumina ratio is greater than 500.

12. A process for isomerization of xylenes which comprises charging hydrogen and a hydrocarbon mixture consisting essentially of aromatic hydrocarbons having eight carbon atoms and paraffin hydrocarbons of 3–12 carbon atoms having no branching in excess of one methyl group on any carbon atom to contact with a zeolite catalyst at a temperature of about 600°–800° F., a pressure above about 100 pounds per square inch and a weight hourly space velocity between 1 and about 200, said zeolite catalyst having a constraint index of 1 to 12, a silica to alumina ratio greater than 12 and a reduced acidity such that less than 2 weight percent of xylene is converted to other compounds when contacted with said catalyst at 900° F., 200 psig and LHSV of 5.

13. The process of claim 12, wherein said zeolite is in the acid form.

14. The process of claim 12, wherein said silica to alumina ratio is greater than 200.

15. The process of claim 12, wherein said silica to alumina ratio is greater than 500.

16. The process of claim 12, wherein said zeolite has been steamed to achieve said reduced activity.

17. The process of claim 12, wherein said zeolite is composited with an inert matrix material in an amount such that the inert matrix constitutes at least 90% of the composite.

18. The process of claim 12, wherein said zeolite contains alkali metal cations.

19. The process of claim 12, wherein said paraffin hydrocarbon is n-nonane.

20. A process according to claim 12, wherein said paraffin hydrocarbon has more than six carbon atoms.

21. A process according to claim 12, wherein said catalyst also contains a Group VIII metal.

22. A process according to claim 21, wherein said metal is platinum.

23. A process according to claim 16, wherein said zeolite has been steamed to an Alpha value of 45–110.

* * * * *